United States Patent [19]

Cassell et al.

[11] 4,415,355

[45] Nov. 15, 1983

[54] DINITROANILINE HERBICIDAL COMPOSITIONS CONTAINING FREEZING POINT DEPRESSANT ADDITIVES

[75] Inventors: Ronald L. Cassell, New Palestine, Ind.; Thomas N. Hall, Baton Rouge, La.

[73] Assignee: BASF Wyandotte Corporation, Wyandotte, Mich.

[21] Appl. No.: 298,648

[22] Filed: Sep. 1, 1981

[51] Int. Cl.³ ............................................. A01N 25/22
[52] U.S. Cl. ................................. 71/121; 71/DIG. 1
[58] Field of Search ........................... 71/121, DIG. 1

[56] References Cited

U.S. PATENT DOCUMENTS

| | | | |
|---|---|---|---|
| 4,163,662 | 8/1979 | Baker, Jr. | 71/120 |
| 4,174,960 | 11/1979 | Hendriksen | 71/121 |
| 4,213,776 | 7/1980 | Giilck et al. | 71/117 |
| 4,288,385 | 9/1981 | Lutz et al. | 71/121 X |

OTHER PUBLICATIONS

Japanese Kokai 78,148,525, Chem. Abst., vol. 91 (1979) 152781x.

*Primary Examiner*—Catherine L. Mills
*Attorney, Agent, or Firm*—David L. Hedden; Joseph D. Michaels

[57] ABSTRACT

The subject invention relates to herbicidal compositions comprising a dinitroaniline compound and a freezing point depressant compound selected from the group consisting of butyrolactone, N,N-dimethylformamide, and mixtures thereof.

The compositions described herein are used as preemergent herbicides and are particularly useful in the control of grasses and broad-leaf weeds for crops such as cotton, soy beans, and peanuts. The freezing point of the dinitroaniline compound is lowered by the addition of the freezing point depressant additive without having a detrimental effect on the activity of the dinitroaniline, the crop, or the environment.

6 Claims, No Drawings

DINITROANILINE HERBICIDAL COMPOSITIONS CONTAINING FREEZING POINT DEPRESSANT ADDITIVES

BACKGROUND OF THE INVENTION

1. Field of the Invention

The subject invention relates to dinitroaniline herbicidal compositions containing freezing point depressant additives. The freezing point depressant additives are selected from a group consisting of butyrolactone, N,N-dimethylformamide, and mixtures thereof.

2. Description of the Prior Art

Dinitroaniline compounds are well known for their use as herbicides. Dinitroaniline compounds such as 2,4-dinitro-4-trifluoromethylaniline are of particular interest and are described in U.S. Pat. No. 4,042,628. These compounds are solids at room temperature. Consequently, in order for them to be useful, they must be dissolved in a solvent to reduce their strength so they can be applied to crops.

One serious problem with the commercially-available herbicidal compositions containing dinitroaniline compounds is that the dinitroaniline compound will crystalize at low temperatures. Dissolving the crystallized dinitroaniline compound after it precipitates is difficult, time consuming, and wasteful. New herbicidal compositions which eliminate this problem and do not have a detrimental effect on the dinitroaniline compound, the crop, and the environment would be of great benefit to the users of these products.

SUMMARY OF THE INVENTION

The subject invention relates to herbicidal compositions comprising

A. a dinitroaniline compound having the following structural formula:

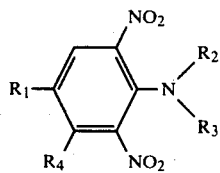

wherein $R_1$ is a radical selected from the group consisting of methyl and trifluoromethyl; $R_2$ is a radical selected from the group consisting of hydrogen, cycloalkyl, and lower alkyl radicals, either straight chain or branched, having 1 to 5 carbon atoms; $R_3$ is a radical selected from the group consisting of lower alkyl, lower chloroalkyl, and lower cyanoalkyl radicals, said radicals being either straight chain or branched and having 1 to 5 carbon atoms; and wherein $R_4$ is a radical selected from the group consisting of methyl and hydrogen; and B. a freezing point depressant compound selected from the group consisiting of butyrolactone, N,N-dimethylformamide and mixtures thereof.

The compositions described herein are used as pre-emergent herbicides and are particularly useful in the control of grasses and broad-leaf weeds for crops such as cotton, soy beans, and peanuts. The freezing point depressant additive can be mixed with the dinitroaniline compound to lower the freezing point of the dinitroaniline compound without having a detrimental effect on the activity of the dinitroaniline compound, the crop, or the environment.

DESCRIPTION OF THE PREFERRED EMBODIMENT

The herbicidal compositions are prepared by mixing dinitroaniline compound and the freezing point depressant compound. Preferably other ingredients such as emulsifiers and solvents are combined with the dinitroaniline compound and the freezing point depressant additive.

The dinitroaniline compounds which are used to prepare the herbicidal compositions are represented by the following structural formula:

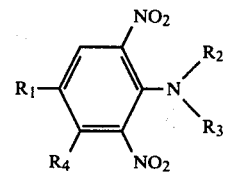

wherein $R_1$ is a radical selected from the group consisting of methyl and trifluoromethyl, $R_2$ is a radical selected from the group consisting of hydrogen, cycloalkyl, and lower alkyl radicals, either straight or branched, having 1 to 5 carbon atoms; $R_3$ is a radical selected from the group consisting of lower alkyl, lower chloroalkyl, and lower cyanoalkyl radicals, said radicals being either straight chain or branched and having 1 to 5 carbon atoms; and wherein $R_4$ is a radical selected from the group consisting of methyl and hydrogen. Preferably used as the dinitroaniline compound are fluchloralin which is N-(2-chloroethyl)-2 6-dinitro-N-propyl-4-(trifluoromethyl)aniline, pendimethalin which is N-(1-ethylpropyl)-3,4-dimethyl-2,6-dinitroaniline, trifluralin which is 3-methyl-4-(trifluoromethyl)-2,6-dinitro-N,N-dipropyl-aniline, and profluralin which is N-(cyclopropylmethyl)-3-methyl-4-(trifluoromethyl)-2,6-dinitro-N-propyl-aniline. The amount of dinitroaniline compound which is used in the herbicidal composition is from 35 to 55 weight percent based on the total weight of the composition.

The freezing point depressant additive which is used in the herbicidal composition is selected from the group consisting of butyrolactone, N,N-dimethylformamide, and mixtures thereof. The amount of freezing point depressant additive used in the herbicidal composition is from 1 to 15 weight percent based on the total weight of the herbicidal composition.

The herbicidal compositions of this invention preferably contain a solvent, emulsifier, or both. Preferably used as solvents are aromatic hydrocarbons, such as xylenes, toluene, benzene or alkyl naphthalenes, chlorinated aromatic or aliphatic hydrocarbons such as chloroethylenes or methylene chloride; aliphatic hydrocarbons, such as cyclohexane or paraffins, for example mineral oil fractions, alcohols, such as butanol or glycol as well as their ethers and esters; ketones, such as acetone, methyl ethyl ketone, methyl isobutyl, ketone or cyclohexanone. Preferred examples of emulsifiying and foam-forming agents include non-ionic ad anionic emulsifiers, such as polyoxyethylene-fatty acid esters, polyoxyethylene-fatty alcohol ethers, for example alkylarylpolyglycol ethers, alkyl sulfonates, alkyl sulfates and aryl sulfonates as well as albumin hydrolyzation products. The total amount of solvent and emulsifier used is from 20 to 45 weight percent based upon the total weight of the herbicide composition.

Other optional ingredients may also be added to the herbicidal composition such as dispersing agents such as lignin, sulfite, waste liquors, and methyl cellulose.

The examples which follow will serve to illustrate the practice of this invention, but are in no way intended to limit its application. The parts referred to in the examples which follow are by weight unless otherwise designated, and the temperatures are in degrees Centigrade unless otherwise designated. The following abbreviations will be utilized in the examples which follow:

FCA—is fluchloralin which is N-(2-chloroethyl)-2,6-dinitro-N-propyl-4-(trifluoromethyl)aniline.
BRL—is butyrolactone.
DMF—is N,N-dimethylformamide.
SF—is a blend of a nonionic and anionic surfactant which acts as an emulsifier and is a 1:1 weight ratio mixture of Westvaco 709 ad Westvaco 710 which are sold by Westvaco Corporation.
SV—is a solvent containing petroleum fractions, primarily xylene, sold by Tenneco Corporation as Tenneco 500-100.

EXAMPLES

Several herbicidal compositions were prepared. The specific ingredients and amounts used are provided in Table I which follows. Note that in the Comparison Example, no freezing point depressant additive was added to the formulation.

TABLE I

| | (Formulations) | | | | | | |
|---|---|---|---|---|---|---|---|
| | Ingredients (Amounts) | | | | | Freezing Point | |
| Examples | FCA | SF | SV | BRL | DMF | Unseeded | Seeded |
| Comparison | 160 | 14 | 26 | — | — | −18° C. | −8° C. |
| 1 | 160 | 14 | 24 | 2 | — | −36° C. | −21° C. |
| 2 | 160 | 14 | 23 | 3 | — | −36° C. | −28° C. |
| 3 | 160 | 14 | 22 | 4 | — | −46° C. | −31° C. |
| 4 | 160 | 14 | 20 | 6 | — | −46° C. | −33° C. |
| 5 | 160 | 14 | 16 | 10 | — | −46° C. | −33° C. |
| 6 | 160 | 14 | 24 | — | 2 | −20° C. | −15° C. |
| 7 | 160 | 14 | 18 | — | 8 | −36° C. | −20° C. |
| 8 | 160 | 14 | 12 | — | 14 | — | −23° C. |
| 9 | 160 | 14 | 8 | — | 18 | −47° C. | −27° C. |

Table I also provides the freezing point data for the various compositions. The seeded samples were prepared by taking 10 milligrams of the samples prepared in accordance with the Comparison Example and Examples 1—9 and adding 0.5 milligram of FCA to the solution. The freezing point was determined by ASTM D145-1973. The table illustrates that the freezing point of the herbicidal compositions containing FCA are significantly reduced by the addition of DMF and BRL.

The table shows that the more freezing point depressant additive which is added, the lower will be the freezing point of the herbicidal composition. However, at higher concentrations, greater than 10 weight percent, no advantage is obtained. This result is obtained without destroying the effectiveness of the herbicidal compositions.

The embodiments of the invention in which an exclusive privilege or property is claimed are defined as follows:

1. A herbicidal composition comprising
   A. a dinitroaniline compound having the following structural formula

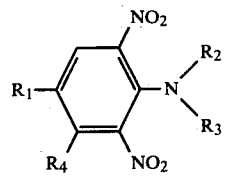

wherein $R_1$ is a radical selected from the group consisting of methyl and trifluoromethyl; $R_2$ is a radical selected from the group consisting of hydrogen, cycloalkyl and lower alkyl radicals, either straight chain or branched, having 1 to 5 carbon atoms; and $R_3$ is a radical selected from the group consisting of lower alkyl, lower chloroalkyl, and lower cyanoalkyl radicals said radicals being either straight chain or branched and having 1 to 5 carbon atoms; and $R_4$ is a radical selected from the group consisting of methyl and hydrogen; and
   B. a freezing point depressant compound selected from the group consisting of butyrolactone, N,N-dimethyl-formamide, and mixtures thereof.

2. The herbicidal composition of claim 1 which contains an emulsifier as an additional ingredient.

3. The herbicidal composition of claim 2 which contains a solvent as an additional ingredient.

4. The herbicidal composition of claim 3 wherein the dinitroaniline compound is N-(2-chlorethyl)-2,6-dinitro-N-propyl-4-(trifluoromethyl)aniline.

5. The herbicidal composition of claim 3 wherein the dinitroaniline compound is selected from the group consisting of N-(2-chloroethyl)-2,6-dinitro-N-propyl-4-(trifluoromethyl)aniline, N-(1-ethylpropyl)-3 4-dimethyl-2,6-dinitroaniline, 3-methyl-4-(trifluoromethyl)-2,6-dinitro-N,N-dipropyl-aniline, and N-(cyclopropylmethyl)-4-(trifluormethyl)-2,6-dinitro-N-propyl-aniline.

6. The herbicidal composition of claim 4 wherein the amount of freezing point depressant additive is from 1 to 10 percent by weight based on the total weight of the composition.

* * * * *

REEXAMINATION CERTIFICATE (488th)
United States Patent [19]
Cassell et al.

[11] B1 4,415,355

[45] Certificate Issued  Apr. 15, 1986

[54] DINITROANILINE HERBICIDAL COMPOSITIONS CONTAINING FREEZING POINT DEPRESSANT ADDITIVES

[75] Inventors: Ronald L. Cassell, New Palestine, Ind.; Thomas N. Hall, Baton Rouge, La.

[73] Assignee: BASF Wyandotte Corporation, Wyandotte, Mich.

Reexamination Request:
No. 90/000,536, Mar. 29, 1984

Reexamination Certificate for:
Patent No.: 4,415,355
Issued: Nov. 15, 1983
Appl. No.: 298,648
Filed: Sep. 1, 1981

[51] Int. Cl.$^4$ ............................................. A01N 33/06
[52] U.S. Cl. ................................. 71/121; 71/DIG. 1
[58] Field of Search ........................... 71/121, DIG. 1

[56] References Cited

U.S. PATENT DOCUMENTS

| | | | |
|---|---|---|---|
| 2,706,677 | 4/1955 | Ducan et al. | 44/71 |
| 2,958,591 | 11/1960 | Jones et al. | 44/63 |
| 3,190,777 | 6/1965 | Breza et al. | 149/57 |
| 4,440,563 | 4/1984 | Scher | 71/88 |

FOREIGN PATENT DOCUMENTS

2900768  7/1979  Fed. Rep. of Germany.

OTHER PUBLICATIONS

Herbicide Handbook of the Weed Science Society of America, pp. 470-476 (Fifth Edition, 1983).
*Organic Solvents* by Riddick and Bunger, pp. 757 and 836-840 (Wiley-Interscience, N.Y., 1971).
40 C.F.R. 180.100(d) (Jul. 1, 1976 issue).
CRC Handbook of Chemistry and Physics, 53rd Edition, p. C-303.
CA 58, 12356(d) (1963).
CA 75, 131460w (1971).
The *Herbicide Handbook of the Weed Science Society of America*, Fourth Edition, 1979, 84-87 and 448.

*Primary Examiner*—Catherine L. Mills

[57] ABSTRACT

The subject invention relates to herbicidal compositions comprising a dinitroaniline compound and a freezing point depressant compound selected from the group consisting of butyrolactone, N,N-dimethylformamide, and mixtures thereof.

The compositions described herein are used as preemergent herbicides and are particularly useful in the control of grasses and broad-leaf weeds for crops such as cotton, soy beans, and peanuts. The freezing point of the dinitroaniline compound is lowered by the addition of the freezing point depressant additive without having a detrimental effect on the activity of the dinitroaniline, the crop, or the environment.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–6 are cancelled.

New claims 7–15 are added and determined to be patentable.

*7. An herbicidal composition comprising:*
*A. a solution of a dinitroaniline compound having the following structural formula*

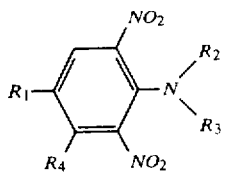

*wherein $R_1$ is a radical selected from the group consisting of methyl and trifluoromethyl; $R_2$ is a radical selected from the group consisting of hydrogen, cycloalkyl and lower alkyl radicals, either straight chain or branched, having 1 to 5 carbon atoms; and $R_3$ is a radical selected from the group consisting of lower alkyl, lower chloroalkyl, and lower cyanoalkyl radicals said radicals being either straight chain or branched and having 1 to 5 carbon atoms; and $R_4$ is a radical selected from the group consisting of methyl and hydrogen; and*

*B. a freezing point depressing amount of butyrolactone.*

*8. The composition of claim 7 which contains an emulsifier as an additional ingredient.*

*9. The composition of claim 7 wherein said dinitroaniline compound is selected from the group consisting of fluchloralin, trifluralin, profluralin, and pendimethalin.*

*10. The composition of claim 7 wherein the amount of butyrolactone is from 1 to 10 percent by weight based upon the total weight of the composition.*

*11. A process for lowering the freezing point of a dinitroaniline herbicide composition comprising adding thereto a freezing point depressing amount of butyrolactone, said dinitroaniline herbicide having the following structural formula*

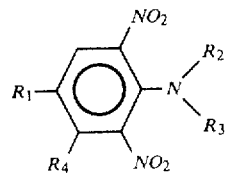

*wherein $R_1$ is a radical selected from the group consisting of methyl and trifluoromethyl; $R_2$ is a radical selected from the group consisting of hydrogen, cycloalkyl and lower alkyl radicals, either straight chain or branched, having 1 to 5 carbon atoms; and $R_3$ is a radical selected from the group consisting of lower alkyl, lower chloroalkyl, and lower cyanoalkyl radicals being either straight chain or branched and having 1 to 5 carbon atoms; and $R_4$ is a radical selected from the group consisting of methyl and hydrogen.*

*12. The process of claim 11 wherein the amount of said butyrolactone is from 1 to 15 percent by weight relative to the weight of the total composition.*

*13. The process of claim 11 wherein the amount of said butyrolactone is from 1 to 10 percent by weight relative to the weight of the total composition.*

*14. In a process for depressing the freezing point of an herbicide solution containing from about 35 percent to about 55 percent by weight relative to the total solution weight of an herbicide compoment consisting essentially of one or more dinitroaniline herbicides having the following structural formula*

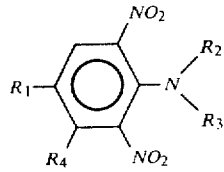

*wherein $R_1$ is radical selected from the group consisting of methyl and trifluoromethyl; $R_2$ is a radical selected from the group consisting of hydrogen, cycloalkyl and lower alkyl radicals, either straight chain or branched, having 1 to 5 carbon atoms; and $R_3$ is a radical selected from the group consisting of lower alkyl, lower chloroalkyl, and lower cyanoalkyl radicals said radicals being either straight chain or branched and having 1 to 5 carbon atoms; and $R_4$ is a radical selected from the group consisting of methyl and hydrogen, wherein the improvement comprises adding thereto a freezing point depressing amount of dimethylformamide.*

*15. The process of claim 14 wherein the amount of said dimethylformamide is from 1 to 10 percent by weight relative to the weight of the total composition.*

* * * * *